United States Patent [19]

Birr

[11] 4,396,605
[45] Aug. 2, 1983

[54] BIS-THYMOSINE α-1 COMPOUNDS

[75] Inventor: Christian Birr, Leimen, St. Ilgen, Fed. Rep. of Germany

[73] Assignee: Max-Planck Gesellschaft Zur Förderung der Wissenschaften e.v., Gottingen, Fed. Rep. of Germany

[21] Appl. No.: 367,817

[22] Filed: Apr. 12, 1982

[30] Foreign Application Priority Data

Sep. 18, 1981 [DE] Fed. Rep. of Germany ....... 3137231

[51] Int. Cl.$^3$ .................... H61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS 4,353,821  10/1982  Birr et al. ..................... 260/112.5 R Primary Examiner—Delbert R. Phillips
Attorney, Agent, or Firm—Felfe & Lynch

[57] ABSTRACT

Bis-thymosine α-1 consisting of two desacetylthymosine α-1 units N-terminally linked by a bridge bond of 1 to 10 carbon atoms, especially an α,ω-diacyl residue with 2 to 10 carbon atoms. This new compound is made by converting a synthetic desacetylthymosine α-1 in which all functional groups of amino acids 1 through 28, except the N-terminal group, are blocked by protective groups conventional in peptide synthesis with a coupling compound of 1 to 10 carbon atoms and that reacts with NH$_2$ groups, in a polar solvent, and then removing the protective groups.

16 Claims, No Drawings

BIS-THYMOSINE α-1 COMPOUNDS

This invention relates to bis-thymosineα-1 compounds, to a process for making same, and to pharmaceutical compositions containing them.

Thymosineα-1 is a peptide that can be isolated from the thymus and which has already been produced synthetically; see German Offenlegungsschrift No. 2 919 592.

Thymosineα-1 stimulates the differentiation and growth T-lymphocytes. It activates the immunodefense cells when added to receptors on their surface. These properties make thymosin especially significant as an immunodefense stimulator, especially against cancer.

It has recently been discovered that the effectiveness of thymosineα-1 can be greatly increased when it is in the form of a twin molecule that retains the monomeric thymosineα-1 structure practically unchanged.

The object of the invention is therefore bis-thymosinα-1 characterized in that it consists of two desacetylthymosineα-1 units that are N-terminally linked by a bridge-type bond with 1 to 10 carbon atoms.

It is assumed that the superior effectiveness of bis-thymosineα-1 derives from the great increase in the concentration of the thymosineα-1 unit at the site of action when the derivative in accordance with the invention is employed.

Preferred embodiments in accordance with the invention have the general formula $$T_2R$$

in which T is a desacetylthymosineα-1 residue and R is a α,ω-diacyl residue with 2 to 10 carbon atoms that can if necessary contain an aromatic nucleus, one or more OH-groups, NH$_2$-groups, halogen atoms, and/or olefinic double bonds or signify a CO-group.

The residue R that bonds the thymosineα-1 residues is preferably derived from phosgene and dicarboxylic acids like oxalic acid, malonic acid, succinic acid, glutaric acid, adipic acid, aspartic acid, glutamic acid, maleic acid, fumaric acid, malic acid, tartaric acid, terephthalic acid, phenylenediacetic acid, and similar compounds. R is more preferably derived from phosgene, oxalic acid, succinic acid, aspartic acid, glutamic acid, maleic acid, or phenylenediacetic acid. Especially preferred is succinyl bis-desacetylthymosineα-1. This compound is derived from thymosineα-1, which is N$^\alpha$-acetylated in its natural form, by replacing a hydrogen atom in the CH$_3$ group of the acetyl residue with a bond to the second thymosineα-1 molecule.

The new bis-thymosineα-1 compounds are manufactured in accordance with the invention by converting a synthetic desacetylthymosineα-1 in which all functional groups of amino acids 1 through 28 except the N-terminal group are blocked by the protective groups common in peptide synthesis with a coupling compound that reacts with NH$_2$ groups and that has 1 to 10 carbon atoms in a polar solvent and then eliminating the protective groups by methods that are in themselves known.

It is practical to proceed from a preliminary stage of synthetic thymosineα-1 in which all functional groups are blocked but the N-terminal acetyl group is missing. It is practical to convert this N-terminally unprotected thymosinα-1 derivative with 0.5 equivalents of the difunctional coupling compound to ensure bis-amidation. Excess blocked desacetylthymosineα-1 can readily be converted to normal thymosineα-1 by acetylation, with acetyl chloride for example. The great difference in molecular weight makes it easy to separate by column chromatography, in trifluoroethanol for example. It can then be converted to the biologically active form by eliminating the protective groups.

Preferred for use as synthetic desacetylthymosineα-1 derivatives with blocked functional groups are Ddz (1-28)-OBzl-thymosineα-1 or Ser(Bzl)-Asp(OBzl)-Ala-Ala-Val-Asp (OBzl)-Thr(Bzl)-Ser(Bzl)-Ser(Bzl)-Glu(OBzl)-Ile-Thr-(Bzl)-Thr-(Bzl)-Lys(Z)-Asp(OBzl)-Leu-Lys(Z)-Glu(OBzl)-Lys(Z)-Lys (Z)-Glu(OBzl)-Val-Val-Glu(OBzl)-Glu(OBzl)-Ala-Glu(OBzl)-Asn-OBzl. These compounds are known from German Offenlegungsschrift 2 919 592 and JACS 101, 253-54 (1979).

If the Ddz protective group-blocked derivative is used, the protective groups are eliminated by treatment with an acid in a polar organic solvent. A trialkylacetic acid like trichloroacetic acid or trifluoroacetic acid is preferred.

Appropriate coupling compounds are difunctional reactive compounds with 1 to 10 carbon atoms. Reactive dicarboxylic-acid derivatives like diactive esters, halogenides, especially chlorides and azides, phosgene, and diepoxides. Typical examples of such reactive dicarboxylic-acid compounds are oxalic acid dichloride, malonic acid dichloride, succinic acid dichloride or anhydride, glutaric acid dichloride, adipic acid dichloride, aspartic acid dichloride, glutamic acid dichloride, maleic or fumaric acid dichloride, malic acid dichloride, tartaric acid dichloride, phthalic acid dichloride, phenylenediacetic acid dichloride, and the analogous derivatives of chlorosuccinic acid, thymidinic acid, suberic acid, azelaic acid, sebacic acid, oxyglytaminic acid, itaconic acid, and racemic acid. The dicarboxylic acids can also be used in their active-ester forms—as p-nitrophenyl, trichlorophenyl, pentachlorophenyl, or pentafluorophenyl esters for example. It is also possible to use the free dicarboxylic acids directly, with (a) a carbodiimide like cyclohexylcarbodiimide or carbonylbisimidazole and (b) benzotriazole.

Dialdehydes derived from the dicarboxylic acids can also be used. The resulting Schiff's base is then hydrated into the secondary amine.

A preferred coupling compound is glutaraldehyde.

Appropriate known conditions are employed for the reaction between the difunctional bridging compound and the amino group of the desacetylthymosinα-1. Examples of appropriate solvents are dimethyl sulfoxide, formamide, and similar compounds and mixtures of them. It is practical for conversion to take place in the presence of an equivalent amount of a base like N-methylmorpholine.

The preparation of the preferred starting materials is described in *Angew. Chemie* 91, 422-23 (1979) and JACS, 253-54 (1979).

The following example will illustrate the invention in detail.

EXAMPLE 50 mg of completely protected thymosineα-1 precursor (10 μmol) Ddz-(1-28)OBzl (MG 5040) produced as described in *Angew. Chemie* 91, 422-23 (1979) were added to 5 ml of dichloromethane being magnetically stirred with 37 μl (475 μmol) of trifluoroacetic acid and kept away from humidity for 1 hour at 20° C. Thin-layer chromatography in a 9:1 mixture of trichloromethane and methyl alcohol indicated elimination of the Ddz protective group as a result of the migrating Ddz fragment. The batch was neutralized with 55 μl (480 μmol) of N-methylmorpholine and evaporated in the vacuum at 40° C. The Ddz fragment was washed from the insoluble with benzine (40° fract.) and the residue dried briefly in the vacuum at 40° C. 5 μl of water were added and the floating flakes of N-terminally free H$_2$N-(1-28)OBzl collected in a centrifuge. The separated peptide was dried in a vacuum over P$_2$O$_5$/KOH and kept for further use.

10 μmol of H$_2$N-(1-28)OBzl were dissolved in 1 ml of dimethylsulfoxide at 40° C., cooled to 0° C., and treated with 1.11 μl (10 μmol) of N-methylmorpholine. A solution of 0.283 μl (2.5 μmol; 0.5 equiv.) of succinyl chloride in 100 μl of dimethylformamide (0° C.) was dripped in in an ultrasonic bath, where the mixture was converted for 1 hour at 0° C. and for 5 hours at 40° C. The batch was cooled to 0° C., treated with 2.22 μl of N-methylmorpholine, and acetylated in the bath with 1.43 μl (20 μmol) of acetyl chloride for 1 hour at 0° C. and for 5 hours at 20°-30° C.

The batch was placed for processing in 160 ml of magnetically stirred water at 0° C. to precipitate the product. After 2 hours the precipitate was suctioned onto a G4 filter and washed with ice water. The resulting filtrate, which was free of salt chloride and acid chloride, was dried over P$_2$O$_5$ and subjected to chromatography with a Sephadex LH20 and trifluoroethanol column (1×200 cm). The protective groups were eliminated by hydrogenolysis in 2,2,2-trifluoroethanol with Pd/C (to eliminate the benzyloxycarbonyl and C-terminal benzylester groups) followed by 30 minutes' subjection to a 1:1 mixture of trifluoroacetic acid and dichloromethane (V/V) containing 10% by volume of anisole (for the t-butylester groups), concentration in the vacuum, and finally treatment with pure trifluoroacetic acid for 2 hours at room temperature (for the 4,4'-dimethoxybenzhydryl and t-butyl groups). The free dimeric N$^\alpha$-succinyl-bis-thymosine$\alpha$-1 (MG 6212) was chromatographically identified and isolated as described there in water (10% trifluoroethanol and 1% acetic acid) on a Riogel P6 column (0.6×240 cm) calibrated for the molecular weight of oxidized insulin B chain (MG 3495) and tested with thymosine$\alpha$-1 (MG 3107).

Thin-layer chromatography showed that the N$^\alpha$-succinyl-bis-thymosin $\alpha$-1 did not migrate (R$_f$=0), while the monomeric thymosine$\alpha$-1 in comparison showed an R$_f$=0.16 (mobile solvent: 5 parts of n-butanol to 5 of pyridine, 1 of glacial acetic acid, and 4 of water, V/V).

It will be understood that the specification and examples are illustrative but not limitative of the present invention and that other embodiments within the spirit and scope of the invention will suggest themselves to those skilled in the art.

What is claimed is:

1. Bis-thymosine$\alpha$-1 compound of the formula

T$_2$R in which
   T is a desacetylthymosine$\alpha$-1 residue,
   R is a $\alpha,\omega$-diacyl residue of 2 to 10 carbon atoms, optionally containing at least one of an aromatic nucleus, OH-groups, NH$_2$-groups, halogen atoms, and olefinic double bonds, or where R is a CO-group.

2. Bis-thymosine$\alpha$-1 compound as claimed in claim 1, wherein R is a $\alpha,\omega$-diacyl residue of 2 to 10 carbon atoms.

3. Bis-thymosine$\alpha$-1 compound as claimed in claim 1, wherein R is a CO-group.

4. Bis-thymosine$\alpha$-1 compound as claimed in claim 1, wherein R is a $\alpha,\omega$-diacyl residue containing an aromatic nucleus.

5. Bis-thymosine$\alpha$-1 compound as claimed in claim 1, wherein R is a $\alpha,\omega$-diacyl residue containing at least one olefinic double bond.

6. Bis-thymosine$\alpha$-1 compound as claimed in claim 1, wherein R is a $\alpha,\omega$-diacyl residue containing at least one of OH, NH$_2$ and halogen.

7. Bis-thymosine$\alpha$-1 compound as claimed in claim 1, wherein R is derived from phosgene.

8. Bis-thymosine$\alpha$-1 compound as claimed in claim 1, wherein R is derived from oxalic acid.

9. Bis-thymosine$\alpha$-1 compound as claimed in claim 1, wherein R is derived from succinic acid.

10. Bis-thymosine$\alpha$-1 compound as claimed in claim 1, wherein R is derived from aspartic acid.

11. Bis-thymosine$\alpha$-1 compound as claimed in claim 1, wherein R is derived from glutamic acid.

12. Bis-thymosine$\alpha$-1 compound as claimed in claim 1, wherein R is derived from maleic acid.

13. Bis-thymosine$\alpha$-1 compound as claimed in claim 1, wherein R is derived from phenylenediacetic acid.

14. Succinyl-bis-desacetylthymosine$\alpha$-1.

15. Pharmaceutical composition for stimulating immuno-defense cells which composition contains a pharmaceutically acceptable carrier and, in effective amount, a bis-thymosine$\alpha$-1 compound as claimed in claim 1.

16. Method of stimulating immuno-defense cells which method comprises administering thereto a pharmaceutically effective amount of a bis-thymosine$\alpha$-1 compound as claimed in claim 1.

* * * * *